(12) United States Patent
Welsch et al.

(10) Patent No.: US 8,030,891 B2
(45) Date of Patent: Oct. 4, 2011

(54) AMBULATORY MEDICAL DEVICE WITH ELECTRICAL ISOLATION FROM CONNECTED PERIPHERAL DEVICE

(75) Inventors: Michael Welsch, Stillwater, MN (US); Michael Treppa, Blaine, MN (US); Russell Kuenzi, St. Louis Park, MN (US); Ronald Dohmen, Plymouth, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 846 days.

(21) Appl. No.: 12/101,001

(22) Filed: Apr. 10, 2008

(65) Prior Publication Data
US 2009/0256527 A1    Oct. 15, 2009

(51) Int. Cl.
*H02J 7/00*    (2006.01)

(52) U.S. Cl. ............ 320/114; 320/112; 607/60; 607/32; 604/27

(58) Field of Classification Search .......... 320/112–114, 320/107
See application file for complete search history.

(56) References Cited

U.S. PATENT DOCUMENTS

| | | | |
|---|---|---|---|
| 3,742,947 A | 7/1973 | Hashem | |
| 5,174,293 A | 12/1992 | Hagiwara | |
| 6,438,420 B1 | 8/2002 | Thompson | |
| 6,617,846 B2 | 9/2003 | Hayat-Dawoodi et al. | |
| 6,820,160 B1 | 11/2004 | Allman | |
| 2002/0007198 A1 | 1/2002 | Haupert et al. | |
| 2003/0200376 A1 | 10/2003 | Engel et al. | |
| 2004/0113498 A1 | 6/2004 | Kroenke | |
| 2005/0001179 A1 | 1/2005 | Gisler et al. | |
| 2005/0113886 A1* | 5/2005 | Fischell et al. .................. 607/60 |
| 2006/0265540 A1 | 11/2006 | Mass et al. | |
| 2007/0055166 A1 | 3/2007 | Patil | |

OTHER PUBLICATIONS

Wikipedia, "Giant Magnetoresistance", Wikipedia Website, www.wikipeida.org, prior to Apr. 10, 2008, 3 Pgs.
Wikipedia, "Infusion Pump", Wikipedia Website, www.wikipedia.org, prior to Apr. 10, 2008, 4 Pgs.
NVE Corporation, IL715 8L716 IL717, "High Speed Four-Channel Digital Isolators", Rev. J, 12 Pgs., © 2005.

* cited by examiner

*Primary Examiner* — Edward Tso
*Assistant Examiner* — Samuel Berhanu
(74) *Attorney, Agent, or Firm* — Patterson Thuente Christensen Pedersen, P.A.

(57) ABSTRACT

Methods and apparatus are provided for electrically isolating an ambulatory medical device for infusing treatment materials into a patient when the medical device is connected to a peripheral device via an active communication cable. In one embodiment, the ambulatory medical device include first circuitry controlling infusion of a medicament to the patient by a fluid conduit connectable to the patient and second circuitry controlling communications when an active communication cable is connected to the medical device. The first and second circuitry are electrically isolated using a pair of first and second isolation transceivers, where the first pair of isolation transceivers communicate a control signal and the second pair of isolation transceivers are giant magneto-resistive (GMR) transceivers that communicate at least one data signal.

11 Claims, 13 Drawing Sheets

AMBULATORY MEDICAL DEVICE WITH ELECTRICAL ISOLATION FROM CONNECTED PERIPHERAL DEVICE

FIELD OF THE INVENTION

The present invention relates generally to improvements for ambulatory medical devices such as devices for introducing treatment material into a body by infusion. More particularly, the invention relates to an ambulatory medical device that is connected by a cable to a peripheral device.

BACKGROUND

As electronic devices become smaller and are used in greater contact with human beings, the importance of electrical safety continually increases. Even relatively small electrical current levels can harm the human body. For example, current levels as low as 60 milliamps (mA) flowing from one hand to the other in a human adult can cause a heart to experience ventricular fibrillation.

Electrical safety is of significant concern in the area of medical devices. Many varieties of electronic medical devices exist that require conductive contact with at least a portion of the human body. Examples of such devices include: ambulatory pumps, pacemakers, electrical leads for delivery of defibrillation pulses or measurement of Electro-CardioGram (ECG) signals, and drug delivery devices. In some circumstances, multiple devices are in conductive contact with the same patient at the same time.

Electrical safety is perhaps of the greatest concern for those devices that are adapted to be placed in contact with intravenous fluids in the human body. This is because the human circulatory system primarily consists of water, which is highly conductive. Electrical safety is a particular concern for devices that are adapted to supply fluid to the human circulator system, because the delivered fluid creates a direct and highly conductive path for harmful currents to reach the human body.

It is often desirable that medical devices be communicatively coupled with a peripheral device such that the device can communicate with the peripheral device to program the device or communicate data and other information. One example of a peripheral device is a personal computer. Some medical devices include a data port that allows an electrical data connection to be made between the medical device and the peripheral device. A medical device may be may be adapted to communicate with a peripheral device using a passive connection or an active connection. A passive connection is one in which electrical signals are transmitted for purposes of communicating data only. In contrast, active devices are those that allow power to be transferred from the peripheral device to the medical device. Examples of passive connections include: RS-232, IEEE 488, Medical Information Bus, Ethernet connection, telephone style connectors, or any other standard or non-standard connector. Examples of active connections include Universal Serial Bus (USB), FireWire, and Power over Ethernet (PoE) connections.

Typically, the danger that exists as a result of the use of electronic devices that are in contact with a patient requires that the medical device be disconnected from contact with the patient in order to connect a peripheral device. This limits a physician or other user, because the removal of the device prevents capture of real-time data from the device while it is connected to the patient. Also, the removal of the device itself may be very cumbersome and time consuming, and may further expose the patient to risk (such as where a needle is removed).

One way in which a medical device can be designed to avoid the hazards associated with electrical medical devices is to electrically isolate the device from the peripheral device. In this context, isolation typically takes the form of translating an electrical signal to some other medium, such as an optical signal, to avoid the transfer of electrical current, and thus the hazards associated with the use of such devices as discussed above.

Some examples of optical isolators are described in the following U.S. Patent documents: US Publ. Appl. No. 2005/0001179 to Gisler et al., U.S. Pat. No. 6,617,846 to Hayat-Dawoodi et al., US Publ. Appl. No. 2004/0113498 to Kroenke, and U.S. Publ. Appl. No. 2006/0265540 to Mass et al., all of which are incorporated by reference in their entirety herein. Optical isolators work by operating one or more light emitting elements (such as a light emitting diode) to transmit light in response to the contents of an electrical signal on one side of the medical device/peripheral device interface. On the other side of the medical device/peripheral device interface, at least some of the transmitted light is collected by a light sensitive electrical device such as a photodiode. The received light is then translated into an electrical current by the light sensitive electrical device. Thus, the original electrical signal is communicated across the medical device/peripheral device interface without conduction of an electrical current. Optical isolators are advantageous in that they provide low-cost and reliable isolation of an electrical signal. However, optical isolators are limited in that they are only capable of effectively isolating an electrical signal transmitted at relatively slower data rates. Therefore, a need exists to provide improved devices and methods providing for a more reliable, higher-speed electrical isolation of signals for use in ambulatory medical devices which utilize active peripheral interface connections.

SUMMARY OF THE INVENTION

The present invention is directed to methods and apparatus for electrically isolating an ambulatory medical device for infusing treatment materials into a patient when the medical device is connected to a peripheral device via an active communication cable. In one embodiment, the ambulatory medical device includes first circuitry controlling infusion of a medicament to the patient by a fluid conduit connectable to the patient and second circuitry controlling communications when an active communication cable is connected to the medical device. The first and second circuitry are electrically isolated using a pair of first and second isolation transceivers, where the first pair of isolation transceivers communicate a control signal and the second pair of isolation transceivers are giant magneto-resistive (GMR) transceivers that communicate at least one data signal.

In various embodiments, the ambulatory medical device includes a housing sized and configured to be ambulatory for a patient. The housing may be constructed to present a communication connector configured to interface with an active communication cable. In various embodiments, the ambulatory medical device includes a fluid conduit configured to be connected to a patient and extend between the housing and the patient. The ambulatory medical device includes a battery carried by the housing that provides electrical power for the device and has a battery ground. In some embodiments, the housing further includes a pump in fluid communication with the fluid conduit. In other embodiments, the housing includes or is adapted to carry as a modular connectable component a reservoir of fluid medicament that is in fluid communication with the pump and/or fluid conduit.

In an embodiment, the ambulatory medical device includes a first circuitry housed within the housing and electrically connected to a ground of the battery. In an embodiment, the first circuitry includes a first isolator transceiver adapted to communicate at least one control signal and a first giant magneto-resistive (GMR) isolator transceiver adapted to communicate at least one electrical data signal, as well as control circuitry having a communication port connected to the first isolator transceiver and the first GMR isolator transceiver. In various embodiments, the communication port is adapted to communicate the at least one control signal and the at least one data signal to and from the control circuitry. In some embodiments, the control circuitry is configured to control operation of a pump housed within the housing of the ambulatory medical device.

In an embodiment, the ambulatory medical device includes second circuitry housed within the housing. In an embodiment, the second circuitry is electrically connected to a cable ground signal on the active communication cable via the communication connector. In an embodiment, the second circuitry includes a second isolator transceiver operably coupled to the first isolator transceiver and adapted to communicate at least one control signal, a second GMR isolator transceiver magnetically coupled to the first GMR isolator transceiver and adapted to communicate at least one data signal, and communication circuitry electrically coupled to a communication connector and to the second isolator transceiver and the second GMR isolator transceiver. In one embodiment, the communication circuitry is adapted to communicate at least one data signal to and from an active communication cable.

The use of electrical isolation in accordance with the various embodiments of the present invention can permit higher communication speeds between an ambulatory medical device and a peripheral device. In some embodiments, the use of GMR isolator arrangements permits the transfer of serial communications at data speeds greater than 12 Mb/sec, speeds which are sufficiently fast enough to keep up with current active communication cable standards, such as USB 2.0.

BRIEF DESCRIPTION OF THE FIGURES

The invention may be more completely understood in consideration of the following detailed description of various embodiments of the invention in connection with the accompanying drawings, in which.

Figure 1:
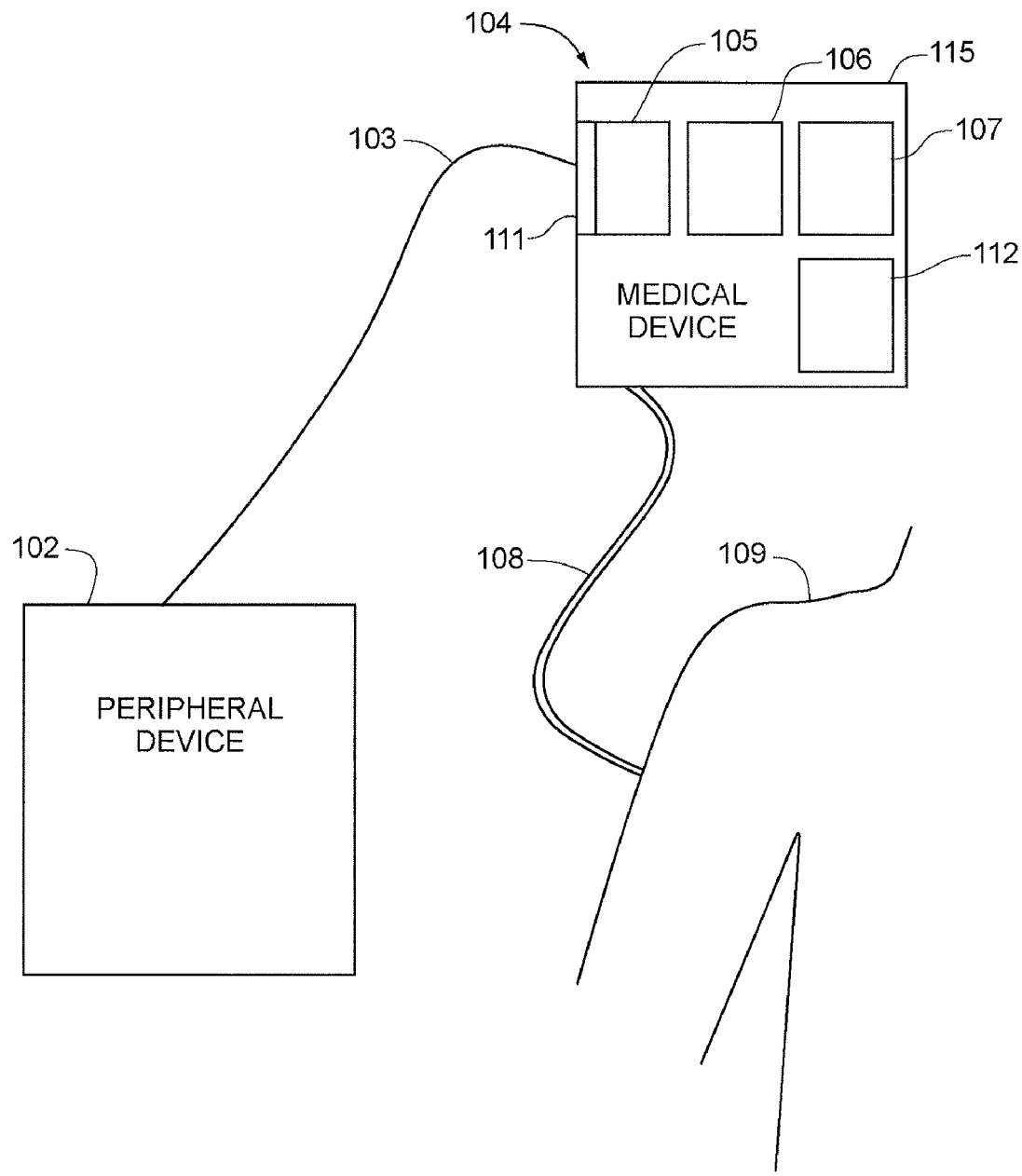
FIG. 1 illustrates generally one example of a known medical device adapted to be communicatively coupled with a peripheral device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENTS

FIG. 1 illustrates generally one example of an electrical medical device 104 in contact with a patient 109 and adapted to be electrically connected to a peripheral device 102. In such an embodiment, medical device 104 may be connectable to a peripheral device via an active communication cable 103. According to this example, medical device 104 may include housing 115. Housing 115 may be sized and configured to be ambulatory for patient 109. Medical device 104 may include communication circuitry 105, processor 106, and one or more medical treatment functions 107. Medical treatment functions 107 may include, for example, one or more sensors or one or more therapy delivery devices. The one or more therapy delivery devices may be adapted to deliver electrical therapy or drug therapy to patient 109. Medical device 104 also includes battery 112. Battery 112 provides electrical power to medical device 104 and has a battery ground.

In various examples, peripheral device 102 is any device capable of communicating with medical device 102. In one example, peripheral device 102 is a computer.

Medical device 104 may be connected to patient 109 through connector 108. In various examples, medical device 104 is adapted to measure, store, and/or communicate device specific or patient specific information to peripheral device 102. In various examples, medical device 102 is adapted to receive and/or transmit data and/or commands from peripheral device 102. In various examples, medical device 104 is electrically connected to peripheral device 102 through communication cable 103 such that peripheral device 102 can communicate with medical device 104.

Medical device 104 may include one or more communication connectors 111. Communication connector(s) 111 may be configured to interface with communication cable 103 such that medical device 104 may be communicatively coupled to peripheral device 102. Communication circuitry 105 may be adapted to communicate with peripheral device 102 using communication cables 103 and communication connectors 111 such as: RS-232, IEEE 488, Universal Serial Bus (USB), Firewire, Medical Information Bus, Ethernet connection, telephone style connectors, or any other standard or non-standard connector. In some examples, communication connector 111 and communication cable 103 support active communication, meaning they are adapted to supply power to medical device 104 through communication cable 103 in addition to providing electrical communication between peripheral device 102 and medical device 104. Examples of active communication cables include USB, Firewire, and powered Ethernet.

Medical device 104 is powered by internal battery 112, and is designed to eliminate any risk of hazardous electrical current from being transferred to patient 109 when medical device 104 is connected to patient 109. However, when medical device 104 is also connected to peripheral device 102 through connector 103, the potential for hazardous electrical current to reach patient 109 exists.

While the example illustrated in FIG. 1 provides a physician or other user the ability to communicate with medical device 104 through electrical connector 103, electrical hazard concerns require that medical device 104 be disconnected from patient 109 in order to connect medical device 104 to peripheral device 102 and communicate with peripheral device 102. This is limiting because a physician or other user is unable to acquire real-time measurements of a patient's conditions or conditions of medical device 104 while medical device 104 is in contact with patient 109. This may be further limiting because medical device 104 must be disconnected and reconnected to patient 109. This may cause injury to patient 109 or may be time consuming or cumbersome. In addition, an already successful procedure may need to be re-performed.

Electrical hazard concerns are significantly important when medical device 104 is placed in fluid contact with patient's 109 circulatory system. This is because a fluid conduit is configured to extend between medical device 104 and patient 109.

It will also be recognized that the communication transfer speeds when using communication cable 103 may not be able to sustain high data transfer rates in accordance with current data transfer standards for many of the communications protocols. For example, if medical device 104 is provided with conventional optical isolation circuitry connected to a USB 2.0 active communication cable, data transfer cannot be sustained at the data transfer rates of up to 12 Mb/second which the USB 2.0 active communication cable would otherwise support.

Figure 2:
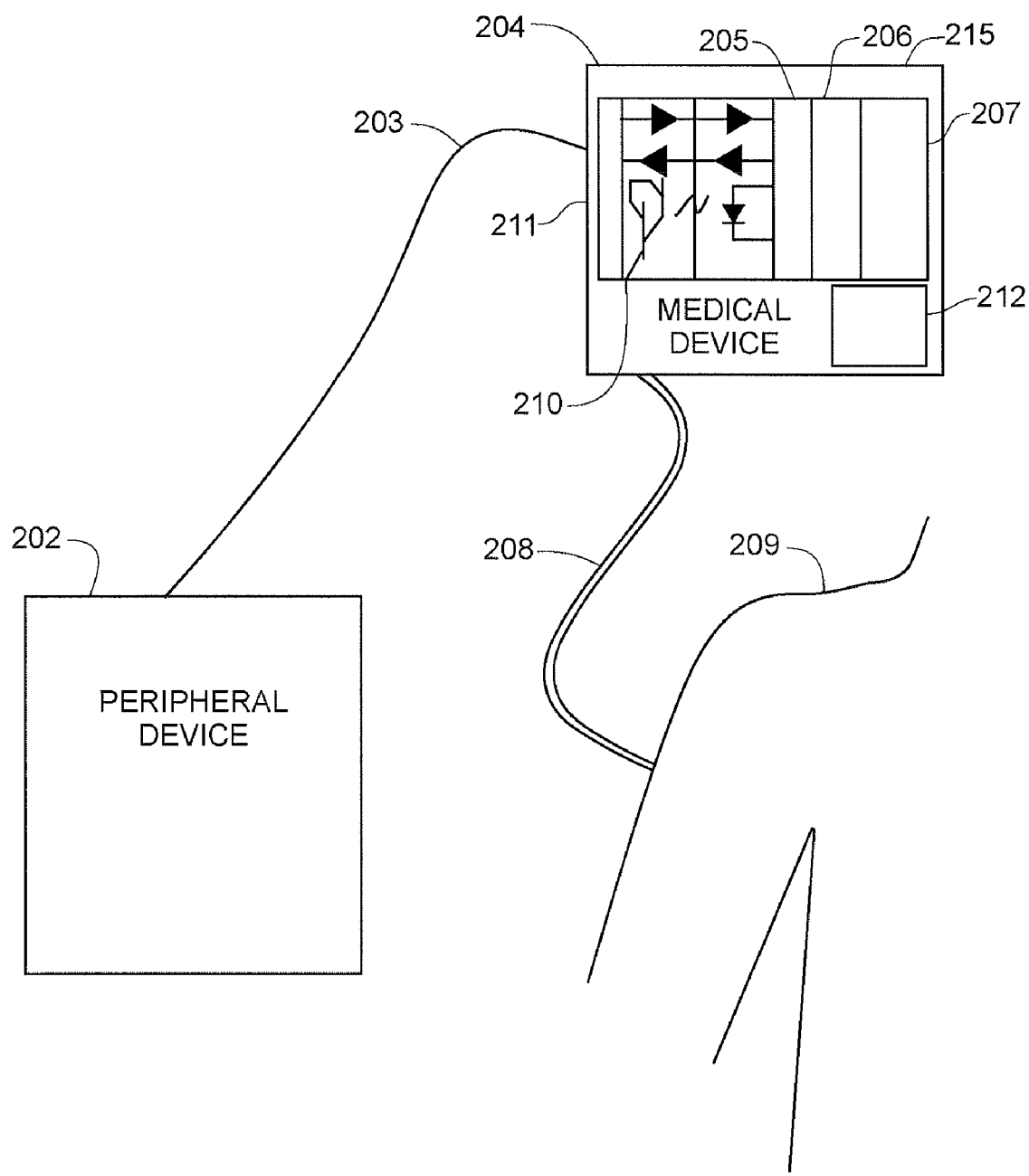
FIG. 2 illustrates generally one embodiment of an isolated medical device according to the subject matter disclosed herein.

FIG. 2 illustrates generally one embodiment of a medical device 204 and peripheral device 202 according to the subject matter disclosed herein. The embodiment illustrated in FIG. 2 is similar to the example of FIG. 1, except medical device 204 further includes isolation circuitry 210. In various embodiments, isolation circuitry 210 is adapted to transmit signals between medical device 204 and peripheral device 202 without transferring any electrical current to medical device 204 that could be potentially harmful to patient 209.

The embodiment illustrated in FIG. 2 is advantageous, because due to isolation circuitry 210, medical device 204 may be electrically connected to peripheral device 202 and remain connected to patient 209 without a risk of harmful electrical currents. Therefore, an electrical connection between medical device 204 and patient 209 does not need to be broken by removing connector 208 from contact with patient 209 to eliminate any electrical hazard concerns. According to the embodiment illustrated in FIG. 2, medical device 104 may communicate with peripheral device 202 without re-performing procedures to connect medical device 204 to patient 209. In addition, peripheral device 202 may communicate with medical device 204 while medical device 204 is connected to patient 209.

Figure 3:
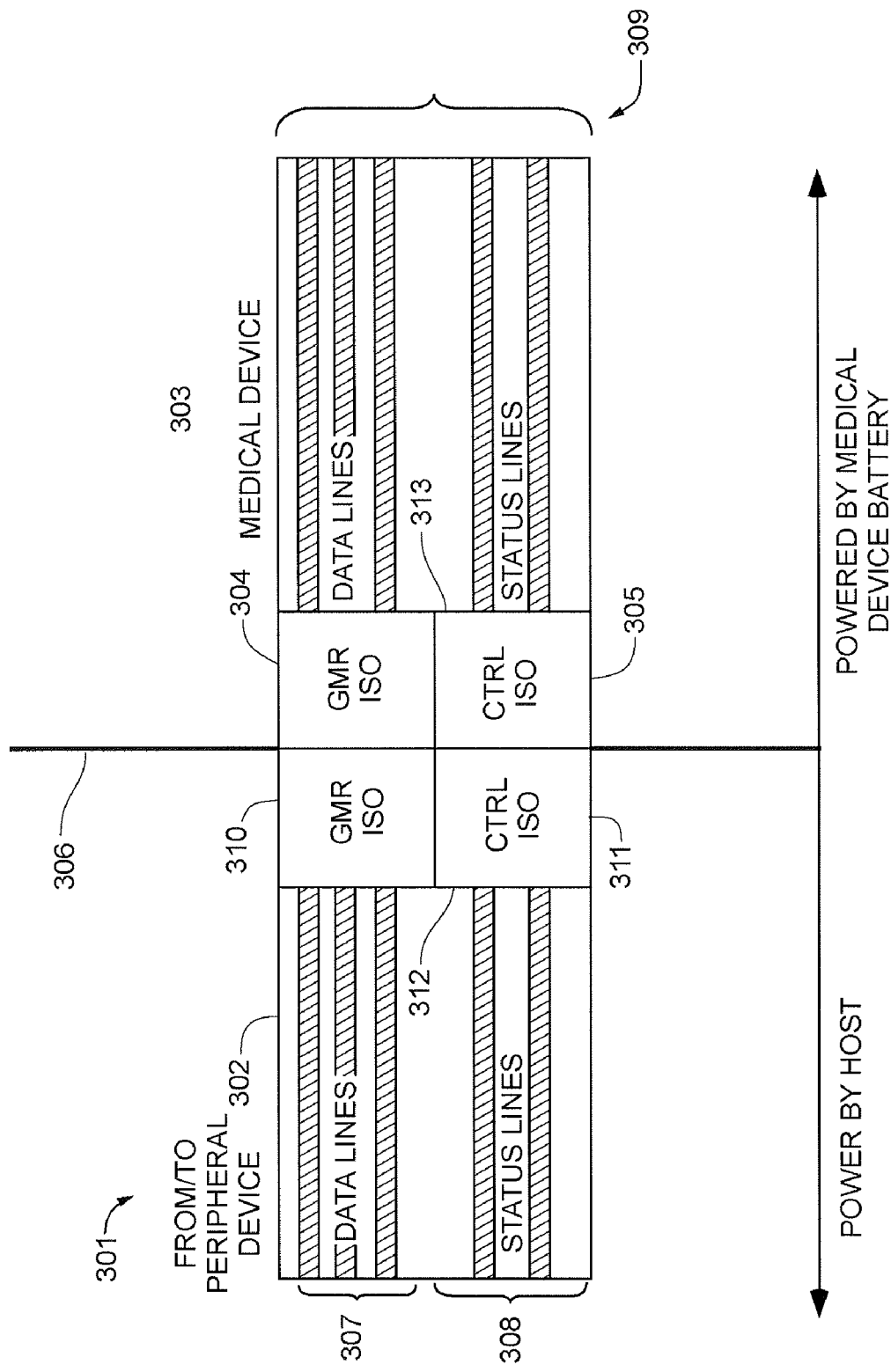
FIG. 3 illustrates generally one embodiment of isolation according to the subject matter disclosed herein.

FIG. 3 illustrates generally one embodiment of isolation circuitry 301 according to the subject matter disclosed herein. According to this embodiment, medical device 303 is adapted to communicate with peripheral device 302 using an active communication cable as discussed with respect to FIG. 1 above.

In various embodiments, information is communicated between medical device 303 and peripheral device 302 over communication lines 309. In various embodiments, medical device includes first isolation circuitry 313 and second isolation circuitry 312. In one embodiment, first isolation circuitry 313 includes isolation transceivers 304 and 305. In one embodiment, first isolation circuitry 313 further includes control circuitry having a communication port connected to isolation transceivers 304 and 305.

In one embodiment, second isolation circuitry 312 includes isolation transceivers 310 and 311. In one embodiment, second isolation circuitry 312 includes control circuitry electrically coupled to isolation transceivers 310 and 311.

In various embodiments, signals transferred between medical device 303 and peripheral device 302 are electrically isolated by isolation transceivers 304, 310 and 305, 311.

In one embodiment, communication lines 309 are split into data lines 307 and status lines 308. Data lines 307 may communicate data between medical device 303 and peripheral device 302. Status lines 308 may communicate a control signal such as information regarding a status of data transmission or information regarding a status of medical device 303 or peripheral device 302 related to data transmissions. In various embodiments, data lines 307 communicate larger amounts of data, or more bits of information, than status lines 308.

In various embodiments, isolation components 304, 305, 310, and 311 are adapted to create a non-electrical signal indicative of an electrical signal on communication lines 309 at a first side of interface 306, and create an electrical signal indicative of the non-electrical signal at a second side of interface 306. Thus, data may be transferred between peripheral device 302 and medical device 303 without any potentially hazardous electrical currents traversing interface 306.

In one embodiment, data lines 307 are electrically isolated by Giant Magneto-Resistive Isolator (GMR isolator) transceivers 310 and 304. GMR isolator transceivers 310 and 304 achieve electrical isolation by changing an electrical resistance at one side of interface 306 in response to a changing magnetic field indicative of an electrical signal at the other side of interface 306.

In one embodiment, GMR isolator transceiver 310 is adapted to receive an electrical signal from peripheral device 302, and initiate or adjust a magnetic field in response to the electrical signal. According to this embodiment, GMR isolator transceiver 304 is adapted to detect the magnetic field, and create an electrical signal based at least in part on the detected magnetic field. In one embodiment, GMR isolator transceiver 304 is adapted to receive an electrical signal from medical device 303, and initiate or adjust a magnetic field in response to the electrical signal. According to this embodiment, GMR isolator transceiver 310 is adapted to detect the magnetic field, and create an electrical signal based at least in part on the detected magnetic field.

The present invention has recognized that a GMR isolator can be advantageous because the GMR isolator can isolate an electrical signal transferred at relatively fast data rates, particularly rates up to and in excess of 12 Mb/sec. However, a GMR isolator is also disadvantageous because in order to accurately transmit isolated data an initial state of the GMR isolator must be known such that the GMR isolator can be reset to or maintained in a known state when a communication is expected. The present invention recognizes and addresses these limitations in the various embodiments as described herein.

In one embodiment, status lines 307 are electrically isolated by isolator transceivers 311 and 305. In one embodiment, isolator transceiver 311 is adapted to receive an electrical control signal, and communicate that control signal in an electrically isolated manner. According to this embodiment, isolator transceiver 305 is adapted to sense the communicated signal, and create an electrical control signal at the medical device 303 side of interface 306. In one embodiment, isolator transceiver 305 is adapted to receive an electrical control signal, and communicate that control signal in an electrically isolated manner. According to this embodiment, isolator transceiver 311 is adapted to sense the communicated signal, and create an electrical control signal at the peripheral device 302 side of interface 306.

In the embodiment illustrated in FIG. 3, GMR isolator transceivers 310 and 304 are used to provide electrical isolation for signals transferred over data lines 307, and control signal isolator transceivers 311 and 305 are used to provide electrical isolation for signals transferred over status lines 308. According to this embodiment, larger amounts of data and faster data rates are required for data line 307 communications. In contrast, smaller amounts of signal transitions and slower transition rates may be required of status line 308 communications.

In various embodiments, first isolation circuitry 313 is housed within housing 215 and is electrically connected to a ground of battery 212. In an embodiment, first isolation circuitry includes first isolator transceiver 305. First isolator transceiver 305 may be adapted to communicate at least one control signal. In an embodiment, first isolation circuitry 313 includes first GNR transceiver 304. First GMR transceiver 304 may be adapted to communicate at least one electrical data signal. In various embodiments, first isolation circuitry 313 further includes a control circuit having a communication port connected to the first isolator transceiver 305 and the first GMR transceiver 304 to communicate the at least one control signal and the at least one data signal to and from the control circuitry.

In various embodiments, second isolation circuitry 312 includes second isolator transceiver 311. In an embodiment, second isolator transceiver 311 is coupled to first isolator transceiver 311 and is adapted to communicate at least one control signal. In various embodiments, second isolation circuitry 312 includes second GMR transceiver 310. In an embodiment, second GMR transceiver 310 is magnetically coupled to first GMR transceiver 304. Second GMR transceiver 310 may be adapted to communicate at least one data signal. In various embodiments, second isolation circuitry 312 includes communication circuitry electrically coupled to communication connector 211, second GMR transceiver 310, and second isolator transceiver 311. In an embodiment, the communication circuitry is adapted to communicate at least one at least one data signal to and from active communication cable 203.

According to various embodiments, control isolator transceivers 311 and 305 provide control signal(s) indicative of a transmission state of data with respect to data lines 307. GMR isolator transceivers 310 and 304 may be reset in response to the control signals. In one embodiment, the control signal(s) are a single bit transmitted through isolator transceivers 311 and 305. In one embodiment, the control signal(s) are multiple bits transmitted through isolator transceivers 311 and 305. In various embodiments, wherein the active power cable is a USB cable, the control signals indicate that the USB cable is connected and that GMR transceivers should prepared to communicate data.

The use of both GMR isolator transceivers 310 and 304 and optical isolator transceivers 311 and 305 as discussed with respect to FIG. 3 is advantageous, because due to the control signal provided by isolator transceivers 311 and 305 over status lines 308, GMR isolator 304 may be reset. Therefore, electrical isolator 301 is able to transmit electrically isolated data at faster data rates without the inaccuracy typically associated with GMR isolators.

Figure 4:
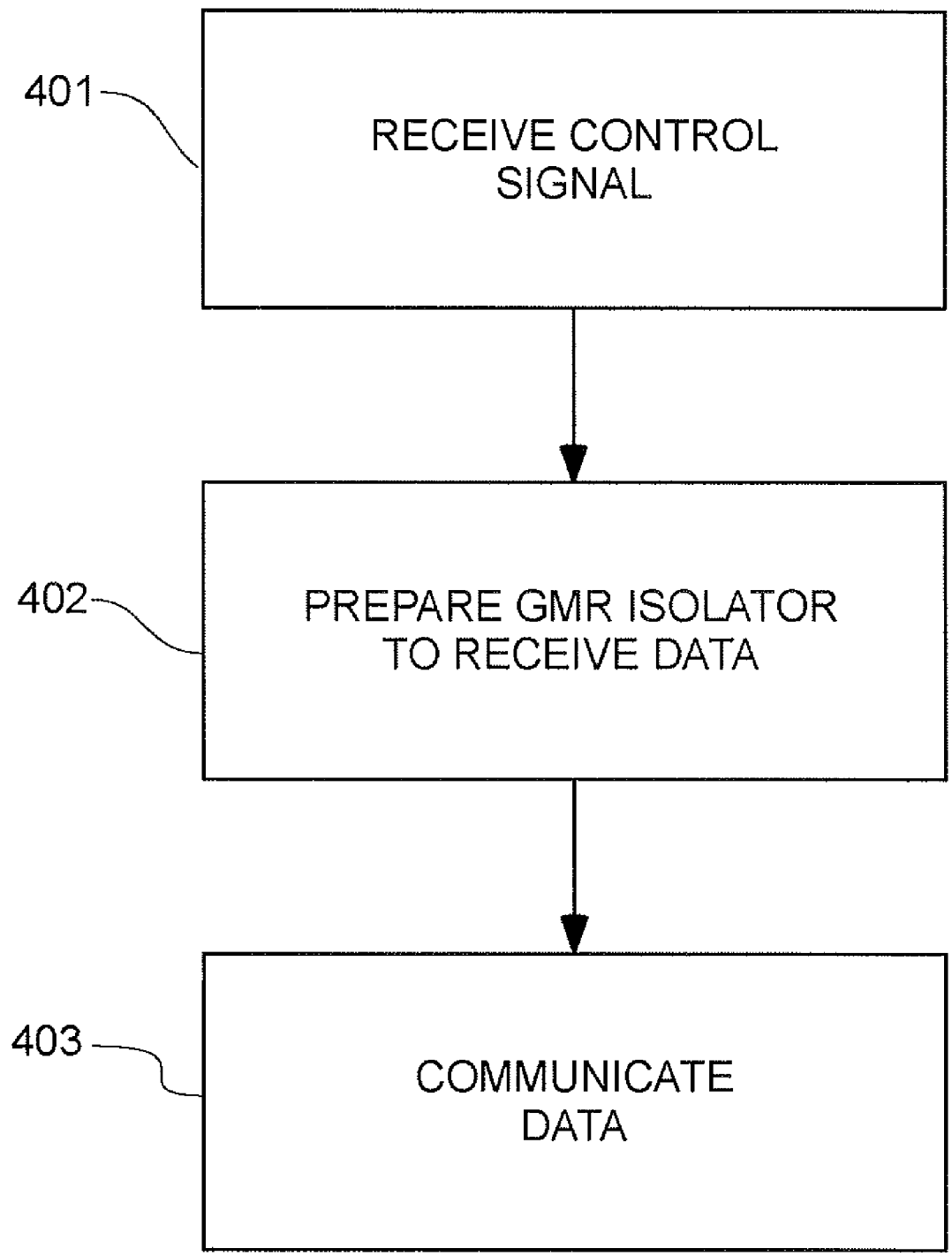
FIG. 4 illustrates generally a flow chart of one embodiment of a method of isolating an electrical signal according to the subject matter disclosed herein.

FIG. 4 illustrates generally a flow chart diagram of one embodiment of a method of signal isolation according to the subject matter described herein. According to the embodiment illustrated in FIG. 4, electrical isolation circuitry 301 is adapted to electrically isolate at least one signal transferred between peripheral device 302 and medical device 303. In one embodiment, the signal may be communicated from peripheral device 302 to medical device 303 across interface 306. In another embodiment, the signal may be communicated from medical device 303 to peripheral device 302 across interface 306.

According to the embodiment illustrated in FIG. 4, at 401, an indication of transmission status is received. In one embodiment, the indication of transmission status is received through isolator transceivers 311 and 305. At 402, GMR isolator transceiver 310 or 304 is prepared to receive data. In one embodiment, preparing the GMR isolator transceiver 310 or 304 to receive data includes modifying a state of GMR isolator transceiver 310 or 304. In another embodiment, preparing the GMR isolator transceiver 310 or 304 to receive data includes maintaining a state of GMR isolator transceiver 310 or 304. At 403, at least one data bit is communicated across GMR isolator transceivers 310 and 304.

Figure 5:
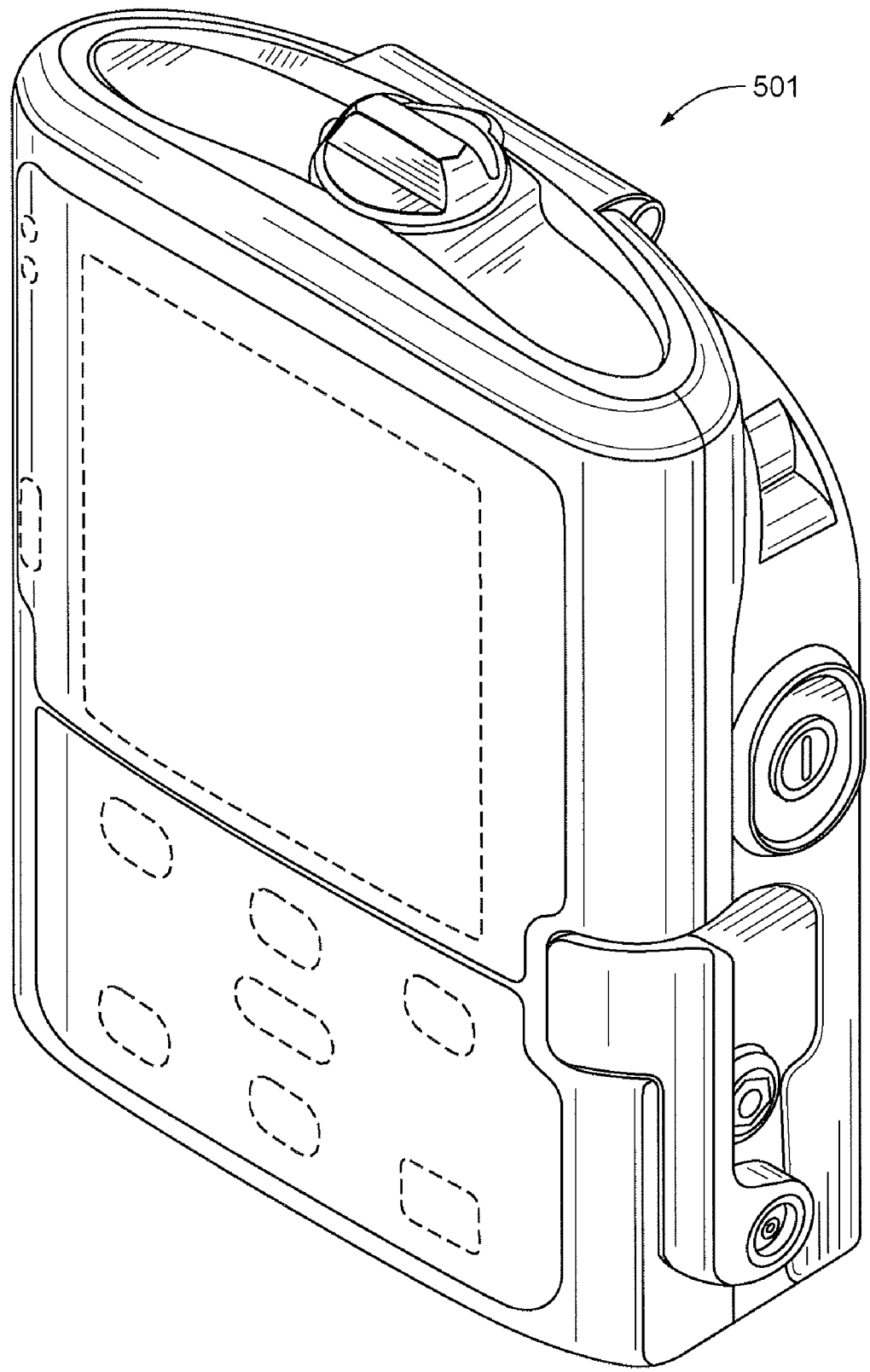
FIG. 5 illustrates generally one example of a medical device according to the subject matter disclosed herein.

FIG. 5 illustrates generally an infusion pump device 501 as the ambulatory medical device according to the subject matter disclosed herein. Infusion pump device 501 is adapted to be connected to a patient circulatory system. Infusion pump device 501 is further adapted to deliver drug therapy to a patient. Drug delivery may occur on a continuous or discreet basis. In other embodiments, the ambulatory medical device may provide dialysis, gene therapy, diabetes treatments or any number of other similar medical treatments where continuous and/or periodic supply of a liquid between the patient and a medical device is part of the medical therapy. In general, it will be understood that the ambulatory nature of the medical device 501 in accordance with the present invention relates to the ability to have the device carried by or mobile with the patient, for example, on a rolling stand, where the medical device is powered, at least in part, by some form of battery or stored energy power supply that is either housed within or carried along with the housing of the medical device. In the embodiment shown in FIG. 5, it will be understood that the infusion pump device is provided with a supply of a liquid-medicament, either in the form of a cassette that is loaded and/or locked within the housing of the infusion pump device, or in the form of a container or bag carried external to the infusion pump device, or even as a separate liquid bag hung, for example, on a rolling medical hanger and connected by inlet tubes to the infusion pump device.

Figure 6:
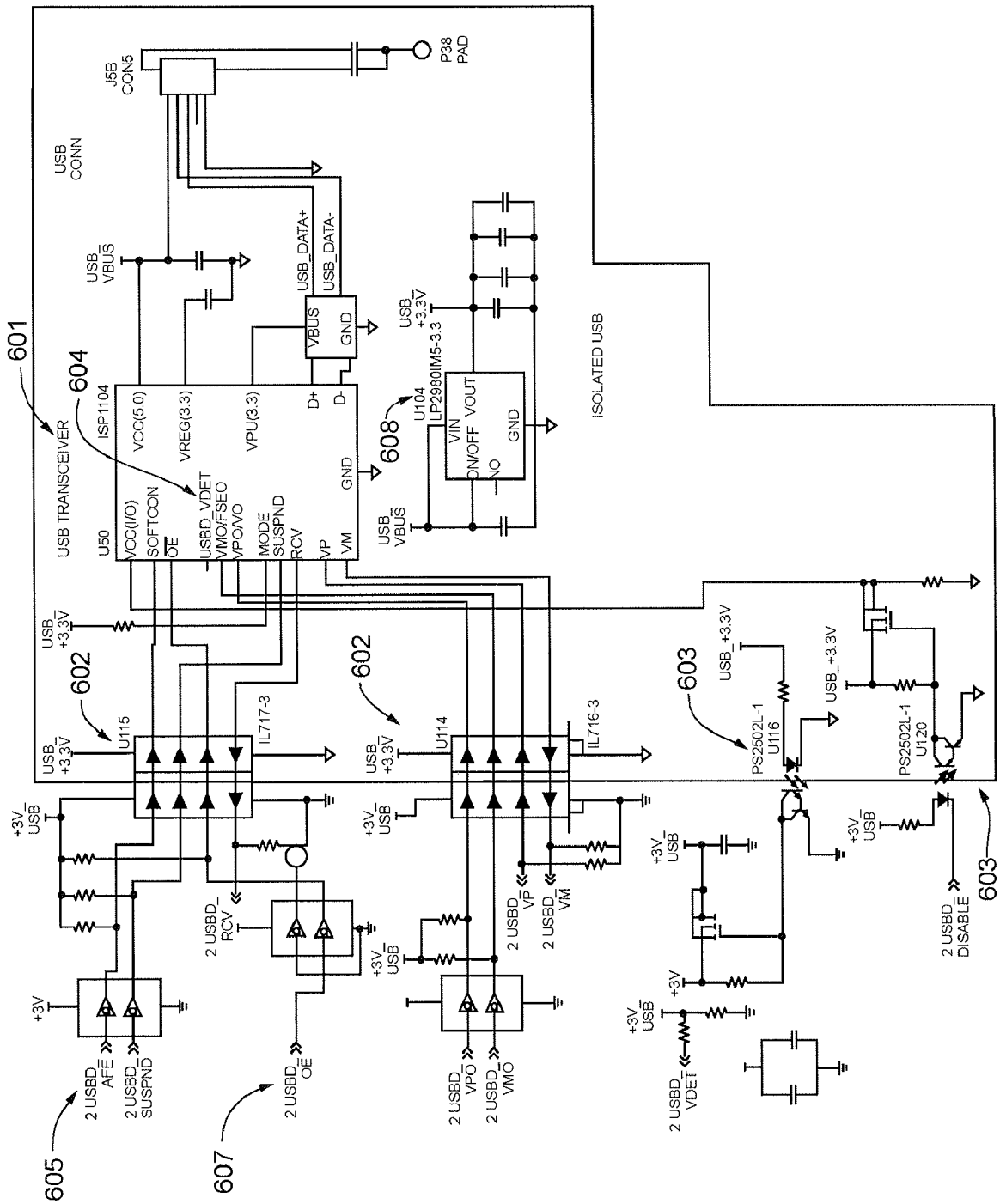
FIG. 6 illustrates generally a circuit diagram of one embodiment of electrically isolated infusion pump circuitry according to the subject matter disclosed herein.

FIG. 6 illustrates generally a circuit diagram of one embodiment of electrically isolated infusion pump circuitry according to the subject matter disclosed herein. According to this embodiment, USB transceiver 601 is adapted to receive and transmit communications. However, USB transceiver must be electrically isolated due to safety concerns. In order to achieve electrical isolation, data signals to or from USB transceiver pass through GMR isolator transceivers 602. As previously discussed with respect to FIG. 3, GMR isolator transceivers are adapted to transmit a signal without any electrical current transfer. The electrical circuit illustrated in FIG. 6 further includes optical isolator transceivers 603. In various embodiments, optical isolator transceivers 503 are adapted to transmit signals indicative of a transmission state of USB transceiver 601 and/or the transmitting portion of GMR transceivers 602. In various embodiments, the receiving portions of GMR transceivers 602 are adapted to be reset in response to the optical signals indicative of a transmission state.

Figure 7:
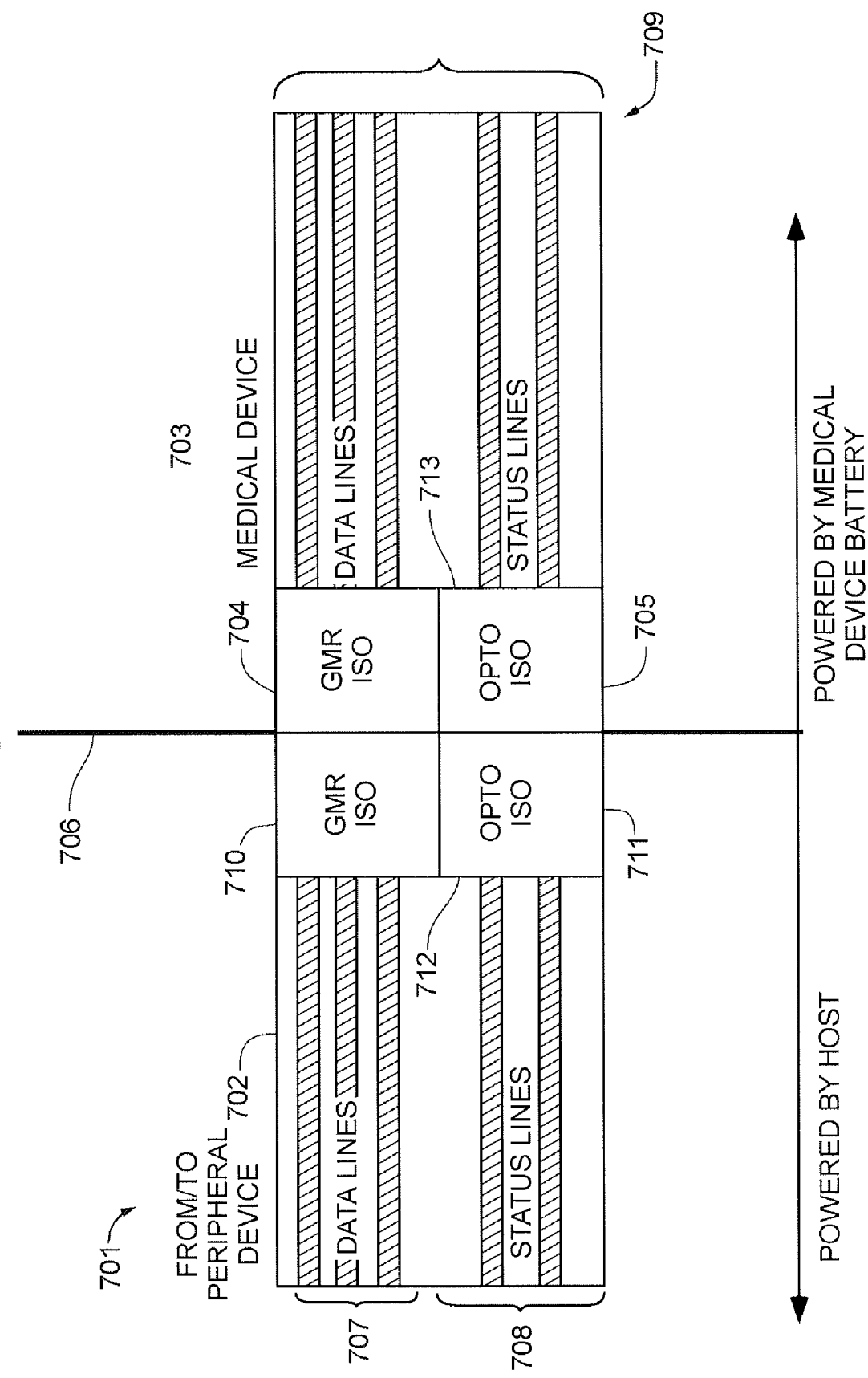
FIG. 7 illustrates generally one embodiment of optical isolation according to the subject matter disclosed herein.

FIG. 7 is a block diagram illustrating generally one embodiment of an isolator including optical isolators according to the subject matter disclosed herein. The embodiment illustrated in FIG. 7 is similar to the embodiment illustrated in FIG. 3, except control isolation transceivers 311 and 305 are optical isolation transceivers.

According to the embodiment illustrated in FIG. 7, status lines 707 are electrically isolated by optical isolator transceivers 711 and 705. Optical isolators are advantageous in that they provide accurate electrical signal isolation.

In one embodiment, optical isolator transceiver 711 is adapted to receive an electrical control signal, and initiate or adjust an optical signal in response to the control signal. According to this embodiment, optical isolator transceiver 705 is adapted to detect the optical signal, and create an electrical control signal at the medical device 703 side of interface 706. In one embodiment, optical isolator transceiver 705 is adapted to receive an electrical control signal, and initiate or adjust an optical signal in response to the electrical control signal. According to this embodiment, optical isolator transceiver 711 is adapted to detect the optical signal, and create an electrical control signal at the peripheral device 702 side of interface 706.

In some embodiments, the control signal received by optical isolator transceivers 711 or 705 is converted to at least one electrical signal. In various embodiments, a controller such as a microprocessor is adapted to receive the electrical signal and modify or maintain a state of GMR isolator transceivers 710 or 704 in response to the received electrical signal. In some embodiments, the transmission state signal received by optical isolator transceivers 711 or 705 is not converted to an electrical signal. According to these embodiments, the at least one optical controller is adapted to receive the optical control signal and modify or maintain a state of GMR isolator transceivers 710 or 704 in response to the received optical signal.

Figure 8:
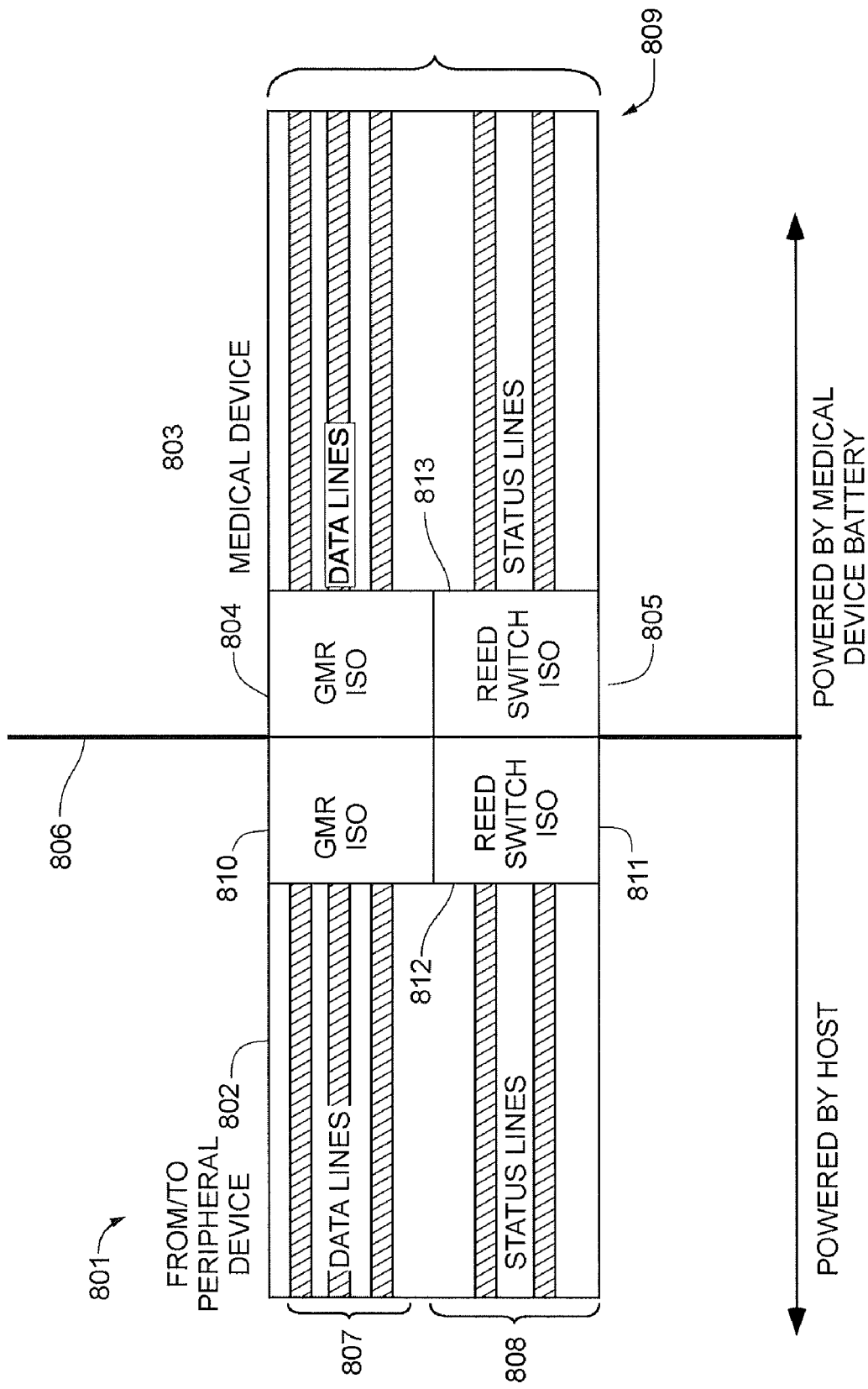
FIG. 8 illustrates generally one embodiment of reed switch isolation according to the subject matter disclosed herein.

FIG. 8 is a block diagram illustrating generally one embodiment of an isolator that includes a magnetic reed switch according to the subject matter disclosed herein. The embodiment illustrated in FIG. 8 is similar to the embodiment illustrated in FIG. 3, except control isolation transceivers 811 and 805 are reed switch isolation transceivers. A reed switch is an electrical switch operated by an applied magnetic field. In various embodiments, a reed switch contains two magnetizable and electrically conductive metal reeds which have end portions separated by a small gap when the switch is open. In one embodiment, an applied magnetic field causes the conductive metal reeds to pull together, thus completing an electrical circuit and allowing a current to flow. In another embodiment, an applied magnetic field causes the conductive metal reeds to pull apart, thus causing current to stop flowing.

In one embodiment, reed switch isolator transceiver 811 is adapted to receive an electrical control signal, and initiate or adjust a magnetic field in response to the control signal. According to this embodiment, reed switch isolator transceiver 805 is adapted to detect the magnetic field, and create an electrical control signal at the medical device 803 side of interface 806. In one embodiment, reed switch isolator transceiver 805 is adapted to receive an electrical control signal, and initiate or adjust a magnetic field in response to the electrical control signal. According to this embodiment, reed switch isolator transceiver 811 is adapted to detect the magnetic field signal, and create an electrical control signal at the peripheral device 802 side of interface 806.

In some embodiments, the control signal received by reed switch isolator transceiver 811 or 805 is converted to at least one electrical signal. In various embodiments, a controller such as a microprocessor is adapted to receive the electrical signal and modify or maintain a state of GMR isolator transceivers 810 or 804 in response to the received electrical signal.

Figure 9:
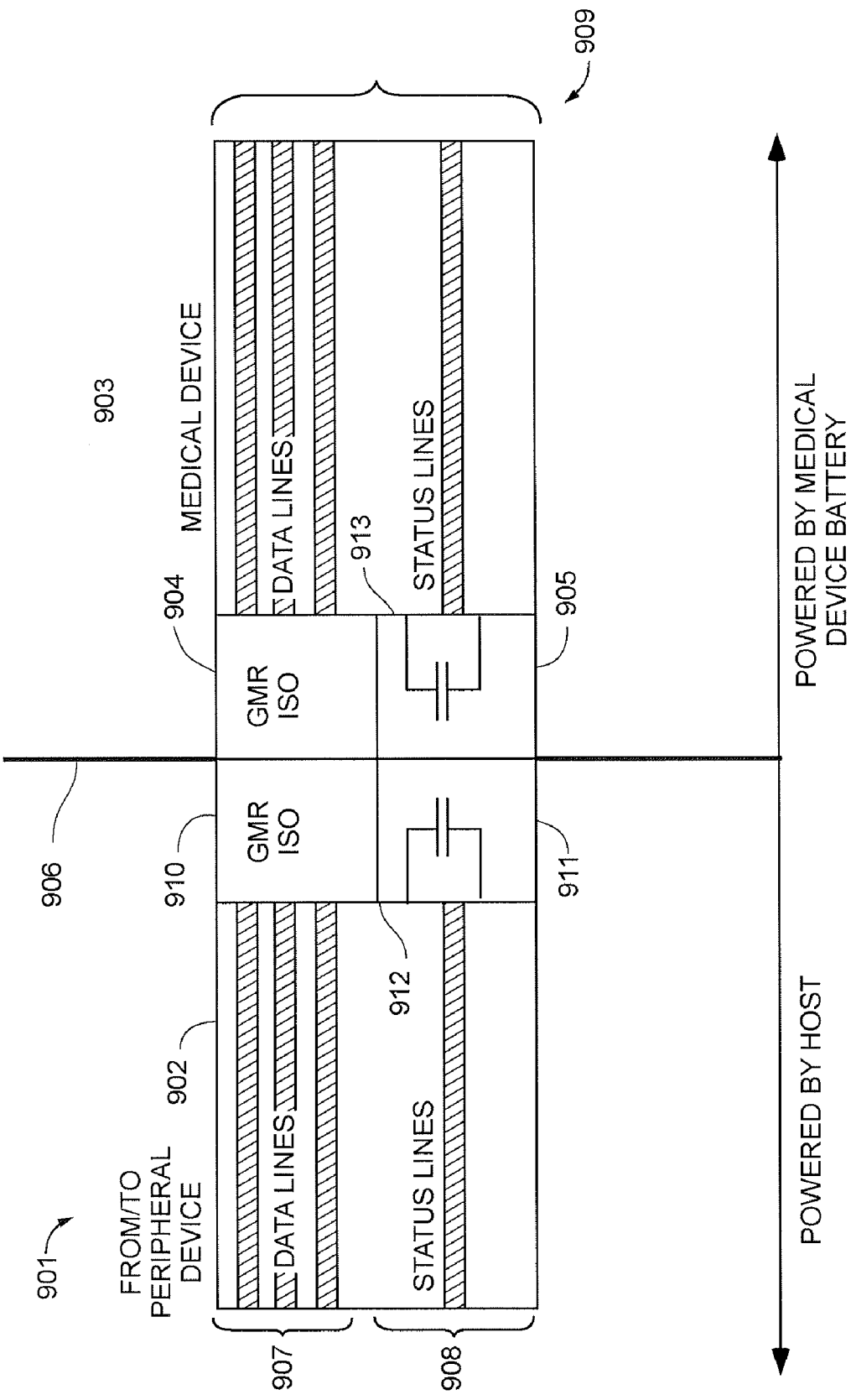
FIG. 9 illustrates generally one embodiment of capacitive coupling isolation according to the subject matter disclosed herein.

FIG. 9 is a block diagram illustrating generally one embodiment of an isolator that includes a capacitive coupling isolator according to the subject matter disclosed herein. The embodiment illustrated in FIG. 9 is similar to the embodiment illustrated in FIG. 3, except control isolation transceivers 911 and 905 are capacitive coupling isolation transceivers. Capacitive coupling is the transfer of energy in an electrical circuit by means of a capacitance between circuit nodes. In various embodiments, capacitive coupling has the effect of connecting two electrical circuits such that low frequency, or DC, components of a signal are removed from the signal. Thus, the voltage amplitude of a signal is greatly reduced while maintaining the higher frequency components of the signal.

According to the embodiment illustrated in FIG. 9, capacitors 911 and 905 are used to isolate control signals transferred over status lines 908. According to this embodiment, an electrical signal at capacitor 911 results in a related electrical signal at capacitor 905. In various embodiments, the amplitude of the related electrical signal at capacitor 905 is greatly reduced compared to the electrical signal at capacitor 911. Thus, according to this embodiment, the electrical control signal may be transferred across interface 906 while greatly reducing the potential for electrical currents that may be harmful to a patient 209.

In various embodiments, a controller such as a microprocessor is adapted to receive the electrical control signal and modify or maintain a state of GMR isolator transceivers 910 or 904 in response to the received electrical signal.

Figure 10:
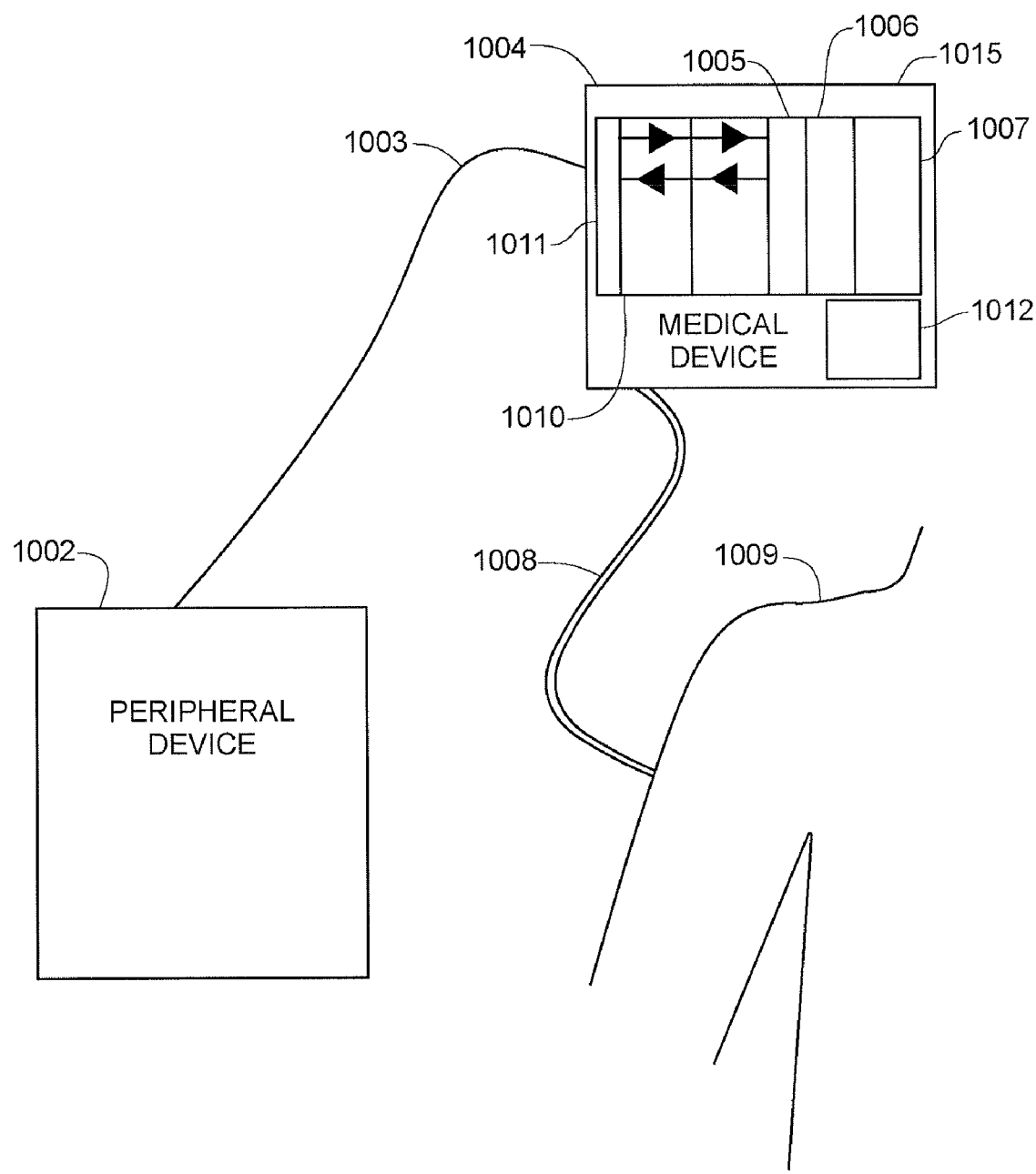
FIG. 10 illustrates generally one embodiment of an isolated medical device adapted to receive a power signal according to the subject matter disclosed herein.

FIG. 10 is a block diagram illustrating generally one embodiment of a medical device that is adapted to be powered by an active communication cable according to the subject matter disclosed herein. The embodiment illustrated in FIG. 10 is similar to the embodiment illustrated in FIG. 2, except medical device 1004 is adapted to be powered by active communication cable 1003.

According to the embodiment of FIG. 10, communication connector 1011 is adapted to provide a power connection to communication cable 1003. In one embodiment, the power connection includes a positive terminal and a ground terminal. In various embodiments, communication connector 1011 includes a positive terminal and a ground terminal. In various embodiments, communication connector 1011 and communication cable 1003 are sized, shaped, and or positioned such that when communication connector 1011 is connected to communication cable 1003 the respective positive and negative terminals are electrically coupled.

In various embodiments, medical device 1004 includes a DC to DC transformer 1010. DC to DC transformer 1010 is a device adapted to transfer electrical energy from a first electrical circuit to a second electrical circuit through inductively coupled electrical conductors. In various embodiments, a changing current at the first electrical circuit creates a changing magnetic field. In various embodiments, the magnetic field induces a changing voltage in the second electrical circuit. If a load is added to the second electrical circuit a current is allowed to flow. Thus, electrical energy is transferred from the first electrical circuit to the second electrical circuit.

According to various embodiments, DC to DC transformer 1010 is adapted to transfer a power signal originating at peripheral device 1002 to medical device 1004 through communicative cable 1003. In various embodiments, DC to DC transformer 1010 is adapted to electrically isolate the power signal by providing a second ground terminal 1020 isolated from the ground terminal of communication connector 1011. Thus, harmful electrical currents are preventing from traversing medical device 1004 and reaching patient 1009.

In various embodiments, power supplied by DC to DC transformer 1010 is used to power components of medical device 1004 such as communication circuitry 1005, processor 1006, and one or more medical treatment functions 1007. In various embodiments, DC to DC transformer 1010 is used to charge battery 1012. In various embodiments, DC to DC transformer 1010 is adapted to modify a voltage level of power supplied to components of medical device 1004.

While the embodiment illustrated in FIG. 10 does not include a control isolation transceiver such as illustrated in FIG. 3, it is to be understood that embodiments that include the supply of active power through DC to DC transformer 1010 and a separate control isolation transceiver are within the scope of the subject matter disclosed herein.

Figure 11:
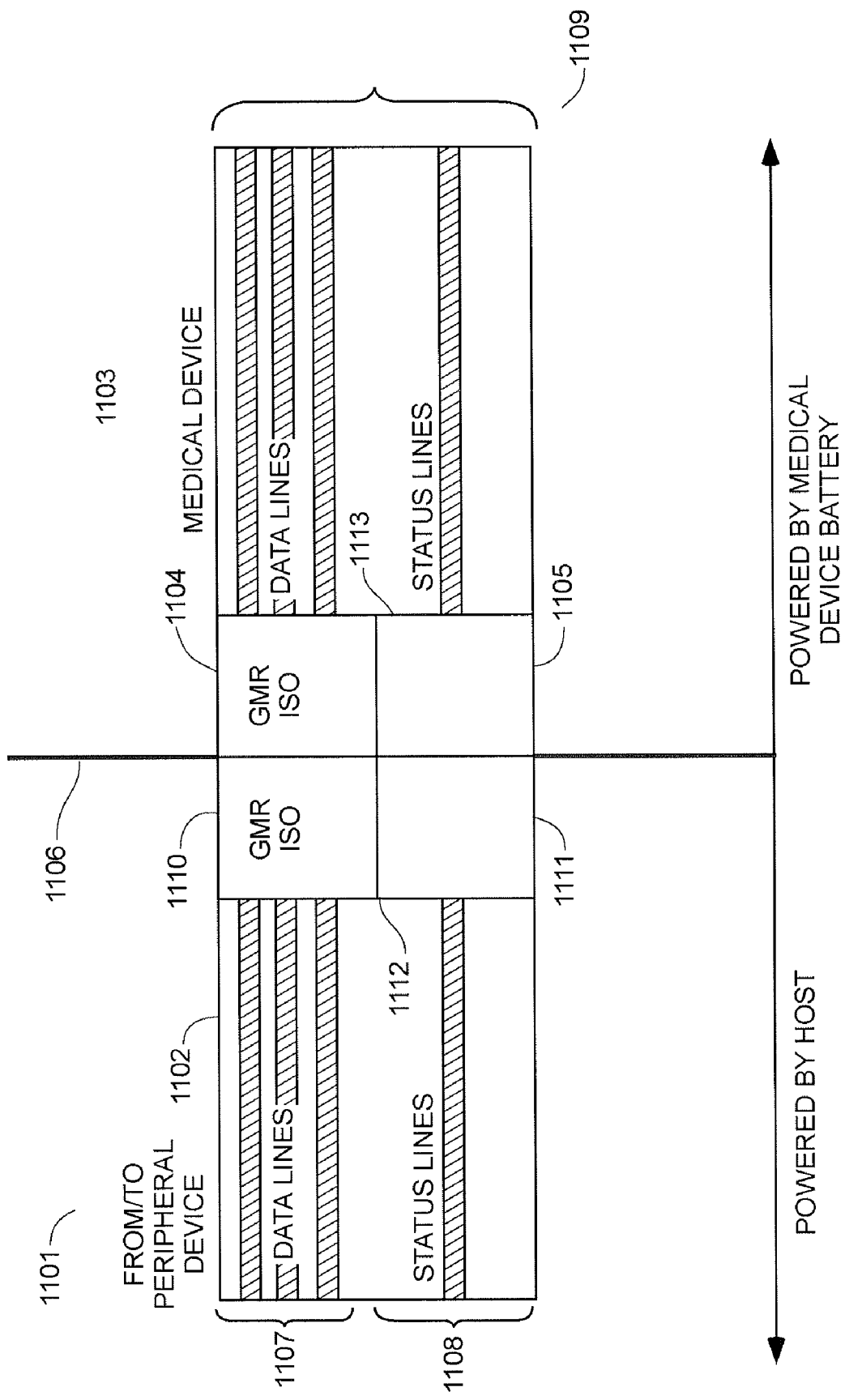
FIG. 11 illustrates generally one embodiment of power supply isolation according to the subject matter disclosed herein.

FIG. 11 is a block diagram illustrating generally one embodiment of a medical device wherein power delivered by an active communication cable is used to transmit a control signal according to the subject matter disclosed herein. The embodiment illustrated in FIG. 11 is similar to the embodiment of FIG. 3, except it includes DC to DC transformer 1111 and 1105. According to this embodiment, DC to DC transformer 1111 and 1105 is used to supply power to components of medical device 1004. In various embodiments, DC to DC transformer 1111 and 1105 is further adapted to communicate at least one control signal across interface 1106. According to these embodiments, in order to properly operate GMR isolator transceivers 1110 and 1104 a transmission state must be known to set GMR isolator transceiver 1110 or 1104 to a known state. According to these embodiments, in order to set detecting portions of GMR isolator transceivers 1110 and 1104, it must be known whether communication cable 1003 is connected to communication connector 1011. According to these embodiments, DC to DC transformer 1111 and 1105 are electrically coupled to at least one control circuit. In various embodiments, the control circuit is adapted to detect whether power is being transferred across DC to DC transformer 1111 and 1105. Thus, the control circuit is able to determine whether communication cable 1003 is connected to communication connector 1011, and whether to set detecting portions of GMR isolator transceiver 1110 or 1104 to receive data transmissions.

Figure 12A:
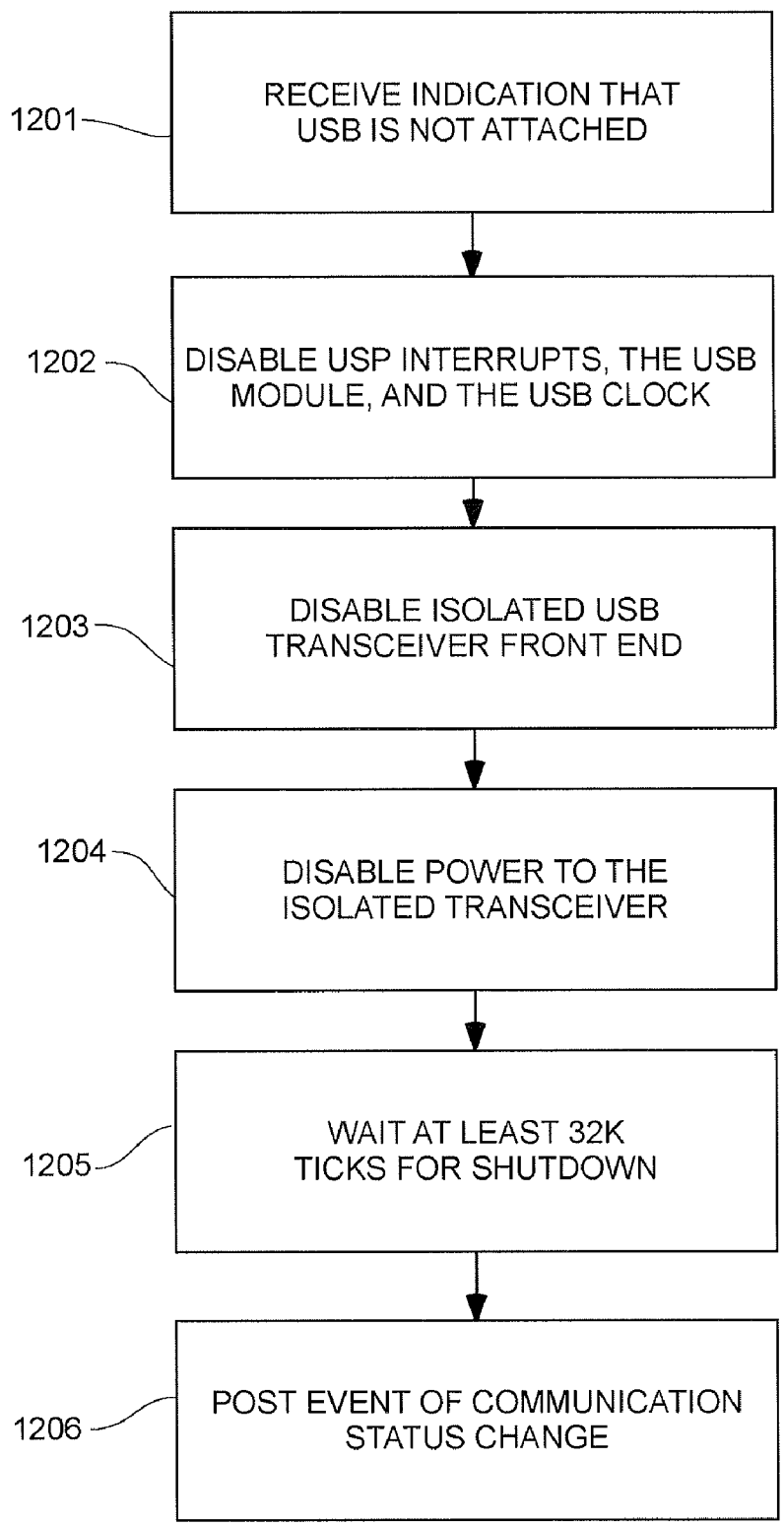
FIG. 12a and FIG. 12b illustrates generally a flow chart diagram of embodiments of operating an isolated medical device according to the subject matter disclosed herein.
Figure 12B:
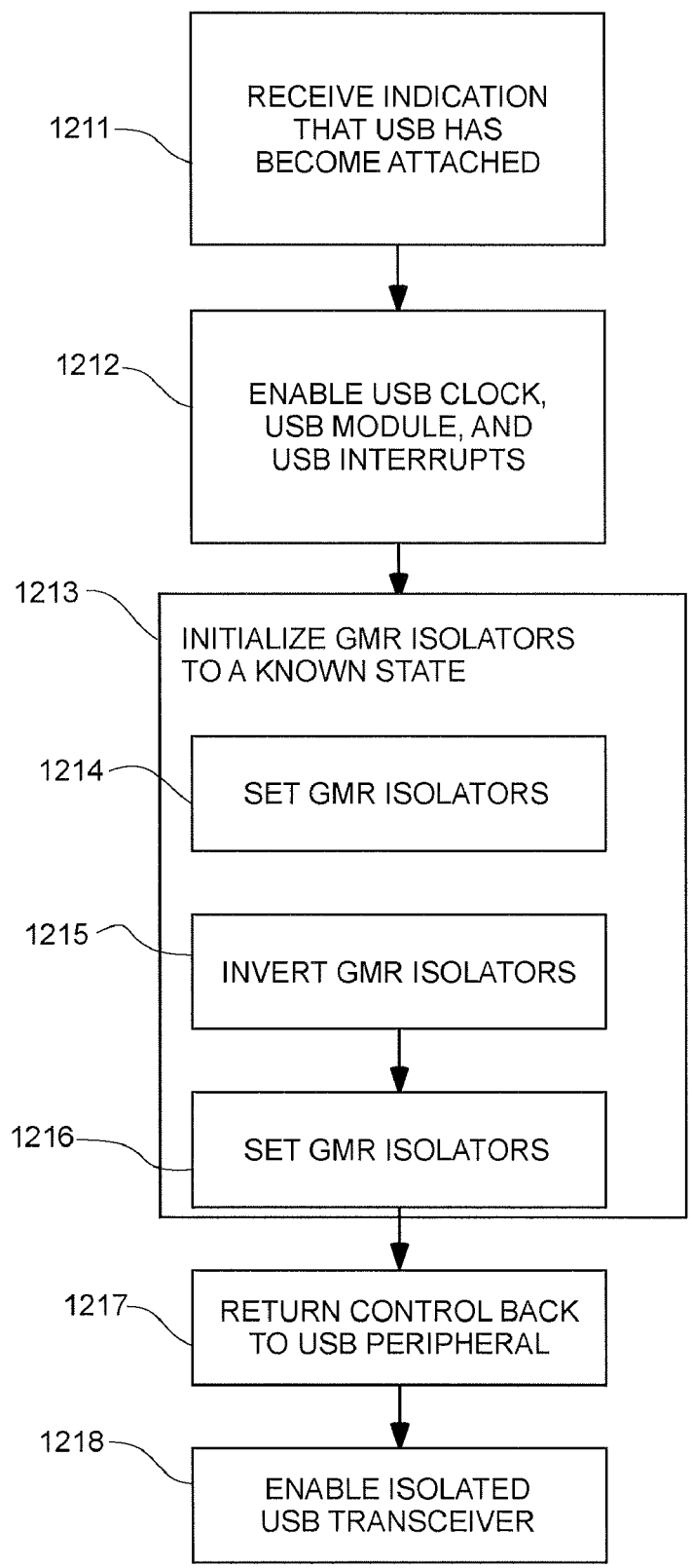

FIG. 12a and FIG. 12b illustrates generally a flow chart diagram of embodiments of operating an isolated medical device according to the subject matter disclosed herein. The embodiments illustrated in FIG. 12a and FIG. 12b and the associated discussion are directed to the circuit illustrated in FIG. 6 for exemplary purposes only. Some exemplary embodiments discussed herein are directed towards integrated circuit component Advanced Universal Serial Bus Transceiver part number ISP 1104 available from Phillips Semiconductors. It is to be understood that these embodiments are presented for exemplary purposes only and alternate embodiments fall within the scope of the subject matter disclosed herein.

FIG. 12a illustrates generally one embodiment of operating the subject matter disclosed herein when communication cable 203 is not connected to medical device 204. According to the embodiment illustrated in FIG. 12a, at 1201 an indication that USB is not attached is received. In one embodiment, receiving an indication that USB is not attached includes detecting that USBD_VDET signal has transitioned from a high state to a low state. In another embodiment, receiving an indication that USB is not attached includes detecting that USBD_VDET signal is in a low state. At 1202, USB interrupts, the USB module, and USB clock of USB transceiver 601 are disabled. At 1203, the USB transceiver 601 analog front-end is disabled. In one embodiment, disabling the USB transceiver 601 analog front-end includes setting USBD_AFE signal 605 to a low state. In one embodiment, at 1204, power to USB transceiver 601 is disabled. In one embodiment, disabling power to the USB transceiver 601 includes setting USB_DISABLE signal 606 to a high state. At 1205, a wait for shutdown function is performed. In one embodiment, waiting for shutdown includes waiting at least 32 k ticks for shutdown. At 1206, the change in communication status event is posted.

FIG. 12a illustrates generally one embodiment of operating the subject matter disclosed herein when communication cable 203 is connected to medical device 204. At 1211, an indication that communication cable 203 has been attached to medical device 204 is received. In one embodiment, receiving an indication that USB is attached includes detecting that USBD_VDET signal 604 has transitioned from a low state to a high state. In another embodiment, receiving an indication that USB is attached includes detecting that USBD_VDET signal 604 is in a high state. In one embodiment, at 1212, USB interrupts, the USB module of a processor, and USB clock of USB transceiver 601 are enabled.

At 1213, GMR isolators are set to a known state. In various embodiments, setting the GMR isolators to a known state includes: 1) at 1214, setting GMR isolators; 2) at 1215, inverting the GMR isolators; 3) at 1216 setting the GMR isolators.

At 1214, setting the GMR isolators includes disabling the isolated USB transceiver 601 analog front end. At 1214, enabling the isolated USB transceiver 601 analog front end includes setting USBD_AFE 605 to a low state. At 1214, setting the GMR isolators 602 includes disabling the USB transceiver 601 output. In one embodiment, disabling the USB transceiver 601 output includes setting USB_OE 607 to a high state.

In one embodiment, at 1215, inverting the GMR isolators 602 includes enabling the USB transceiver 601 analog front-end. In one embodiment, at 1215, enabling the USB transceiver 601 analog front-end includes setting USBD_AFE 605 to a high state. In one embodiment, at 1215, setting the GMR isolators 602 includes enabling the USB transceiver 601 output. In one embodiment, disabling the USB transceiver 601 output includes setting USB_OE 607 to a low state.

In one embodiment, at 1216, setting the GMR isolators 602 includes disabling the USB transceiver 601 analog front-end. In one embodiment, at 1216, enabling the USB transceiver 601 analog front-end includes setting USBD_AFE 605 to a low state. In one embodiment, at 1216, setting the GMR isolators 602 includes disabling the USB transceiver 601 output. In one embodiment, disabling the USB transceiver 601 output includes setting USB_OE 607 to a high state.

At 1217, control is returned to a peripheral device attached to medical device 204 through communication cable 203. In one embodiment, returning control to the peripheral device includes returning control of USBD_AFE 605 and USB_OE 607 signals. At 1218, the USB transceiver 601 is enabled. In one embodiment, enabling the USB transceiver 601 includes setting USB_DISABLE 606 to a low state.

Finally, while the present invention has been described with reference to certain embodiments, those skilled in the art should appreciate that they can readily use the disclosed conception and specific embodiments as a basis for designing or modifying other structures for carrying out the same purposes of the present invention without departing from the spirit and scope of the invention as defined by the appended claims.

The invention claimed is:

1. An ambulatory medical device connectable to a peripheral device via an active communication cable, the ambulatory medical device comprising:
   a housing sized and configured to be ambulatory for a patient and presenting a communication connector configured to interface with the active communication cable;
   a fluid conduit configured to extend between the housing and the patient;
   a battery carried by the housing that provides electrical power for the device and has a battery ground;
   first circuitry housed within the housing and electrically connected to the battery ground, the first circuitry including:
      a first isolator transceiver adapted to communicate at least one control signal;
      a first giant magneto-resistive (GMR) isolator transceiver adapted to communicate at least one electrical data signal; and
      control circuitry for the device having a communication port connected to the first isolator transceiver and the first GMR isolator transceiver to communicate the at least one control signal and the at least one data signal to and from the control circuitry; and
   second circuitry housed within the housing and electrically connected to a cable ground signal on the active communication cable via the communication connector, the second circuitry including:
      a second isolator transceiver coupled to the first isolator transceiver and adapted to communicate the at least one control signal;
      a second GMR isolator transceiver magnetically coupled to the first GMR isolator transceiver and adapted to communicate the at least one data signal; and
      communication circuitry electrically coupled to the communication connector and to the second isolator transceiver and the second GMR isolator transceiver to communicate the at least one data signal to and from the active communication cable, such that the first circuitry and the patient are isolated from the second circuitry and the peripheral device.

2. The device of claim 1, wherein the first and second isolator transceivers are optoisolators.

3. The device of claim 1, wherein the first and second isolator transceivers are reed switches.

4. The device of claim 1, wherein the first and second isolator transceiver comprises a DC-to-DC transformer.

5. The device of claim 1, wherein the first and second isolator transceiver are capacitively coupled isolators.

6. The device of claim 1 wherein the active communication cable is a Universal Serial Bus (USB) 2.0 cable and wherein:
   the first isolator transceiver and the second isolator transceiver comprise:
      a first transmitter coupled to a second receiver to communicate a USB active control signal from the first circuitry to the second circuitry; and
      a first receiver coupled to a second transmitter to communicate a USB active control signal from the second circuitry to the first circuitry; and
   wherein the first GMR isolator transceiver and the second GMR isolator transceivers comprise:
      five first GMR transmitters correspondingly coupled to five second GMR receivers to communicate five USB data signals from the first circuitry to the second circuitry; and
      three first GMR receivers correspondingly coupled to three second GMR transmitters to communicate three USB data signals from the second circuitry to the first circuitry.

7. The device of claim 1, wherein the battery of the ambulatory medical device is a rechargeable battery and wherein the medical device further includes circuitry adapted to permit the rechargeable battery to be recharged via the active communication cable.

8. The device of claim 1, wherein the active communication cable is selected from the group consisting of: Universal Serial Bus communication, Firewire communication, or Powered Ethernet communication.

9. The device of claim 1, wherein the at least one control signal includes an indication that the first GMR isolator transceiver is prepared to initiate or adjust a magnetic field.

10. The device of claim 1, wherein the at least one control signal includes an indication that the second GMR isolator transceiver is to be prepared to detect a magnetic field.

11. A method of electrically isolating a communication of an ambulatory medical device that is connectable to a peripheral device via an active communication cable, comprising:
   providing an ambulatory medical device having a housing containing a communication connector configured to interface with an active communication cable; a battery; a first circuitry housed within the housing and electrically connected to the battery ground, the first circuitry comprising a first isolator transceiver adapted to communicate at least one control signal, a first GMR isolator transceiver adapted to communicate at least one electrical data signal, and a control circuitry for the device having a communication port connected to the first isolator transceiver and the first GMR isolator transceiver to communicate the at least one control signal and the at least one data signal to and from the control circuitry; and a second circuitry housed within the housing and electrically connected to a cable ground signal on the active communication cable via the communication connector, the second circuitry comprising a second isolator transceiver coupled to the first isolator transceiver and adapted to communicate the at least one control signal, a second GMR isolator transceiver magnetically coupled to the first GMR isolator transceiver and adapted to communicate the at least one data signal, and a communication circuitry electrically coupled to the communication connector and to the second isolator transceiver and the second GMR isolator transceiver to communicate the at least one data signal to and from the active communication cable, such that the first circuitry and the patient are isolated from the second circuitry and the peripheral device, the ambulatory medical device further having a fluid conduit configured to extend between the housing and the patient, and providing instructions to couple the active communication cable to the communication connector of the medical device and initiate a data transfer between the medical device and the peripheral device such that the first circuitry and the patient are isolated from the second circuitry and the peripheral device while the active communication cable is connected and the data transfer can occur at a data transfer rate of at least 12 Mb/second.

* * * * *